United States Patent
Vaillancourt et al.

(10) Patent No.: US 10,238,376 B2
(45) Date of Patent: Mar. 26, 2019

(54) WOUND PROTECTOR

(71) Applicants: Michael J. Vaillancourt, Chester, NJ (US); Marshall Kerr, Carlsbad, CA (US); Jeicol Herrera, Morristown, NJ (US)

(72) Inventors: Michael J. Vaillancourt, Chester, NJ (US); Marshall Kerr, Carlsbad, CA (US); Jeicol Herrera, Morristown, NJ (US)

(73) Assignee: VLV Associates, Inc., Whippany, NJ (US)

( * ) Notice: Subject to any disclaimer, the term of this patent is extended or adjusted under 35 U.S.C. 154(b) by 530 days.

(21) Appl. No.: 14/738,223

(22) Filed: Jun. 12, 2015

(65) Prior Publication Data

US 2016/0113641 A1    Apr. 28, 2016

Related U.S. Application Data

(63) Continuation-in-part of application No. 14/523,157, filed on Oct. 24, 2014.

(51) Int. Cl.
*A61B 17/34* (2006.01)
*A61B 17/02* (2006.01)
*A61B 17/00* (2006.01)

(52) U.S. Cl.
CPC ...... *A61B 17/0293* (2013.01); *A61B 17/3423* (2013.01); *A61B 2017/00407* (2013.01); *A61B 2017/00991* (2013.01)

(58) Field of Classification Search
CPC . A61B 17/0218; A61B 17/0206; A61B 17/02; A61B 17/0293; A61B 2017/0237
See application file for complete search history.

(56) References Cited

U.S. PATENT DOCUMENTS

| | | | | |
|---|---|---|---|---|
| 5,640,977 A * | 6/1997 | Leahy | ............... | A61B 17/3423 128/850 |
| 5,667,481 A * | 9/1997 | Villalta | ............... | A61B 17/02 600/219 |
| 6,051,007 A * | 4/2000 | Hogendijk | ............ | A61B 17/08 606/151 |
| 7,052,454 B2 * | 5/2006 | Taylor | ............... | A61B 17/3423 600/114 |
| 7,377,472 B2 * | 5/2008 | Brown | .................... | F16L 3/10 24/16 R |
| 8,366,754 B2 * | 2/2013 | Teague | .............. | A61B 17/8076 24/372 |
| 8,597,180 B2 * | 12/2013 | Copeland | .......... | A61B 17/0218 600/201 |
| 8,864,658 B2 * | 10/2014 | Wilkins | ............. | A61B 17/3423 600/201 |
| 8,961,408 B2 * | 2/2015 | Wilkins | ............. | A61B 17/0293 600/203 |

(Continued)

Primary Examiner — Jacqueline T Johanas
(74) Attorney, Agent, or Firm — Francis C. Hand; Carella, Byrne, Et Al

(57) ABSTRACT

The wound protector has an annularly collapsible distal ring, an expansion member and a flexible sleeve extending between the distal ring and expansion member. After positioning of the distal ring in a wound, movement of the expansion member into an extended state expands the sleeve while drawing the sleeve tight against the wound and the expansion member against the patient.

10 Claims, 6 Drawing Sheets

(56) References Cited

U.S. PATENT DOCUMENTS

| | | | |
|---|---|---|---|
| 8,961,409 B2* | 2/2015 | O'Prey | A61B 17/0293 600/206 |
| 9,039,610 B2* | 5/2015 | Wilkins | A61B 17/0293 600/206 |
| 2002/0004628 A1* | 1/2002 | Hu | A61B 17/02 600/210 |
| 2004/0054353 A1* | 3/2004 | Taylor | A61B 17/3423 606/1 |
| 2004/0186354 A1* | 9/2004 | LiDonnici | A61B 1/32 600/210 |
| 2009/0138083 A1* | 5/2009 | Biyani | A61F 2/44 623/17.11 |
| 2010/0210916 A1* | 8/2010 | Hu | A61B 17/0206 600/210 |
| 2012/0041269 A1* | 2/2012 | Copeland | A61B 17/0218 600/208 |
| 2012/0143008 A1* | 6/2012 | Wilkins | A61B 17/0293 600/206 |
| 2012/0296170 A1* | 11/2012 | Wilkins | A61B 17/0293 600/206 |
| 2013/0150681 A1* | 6/2013 | O'Prey | A61B 17/0293 600/206 |
| 2015/0094541 A1* | 4/2015 | Wilkins | A61B 17/0293 600/204 |
| 2015/0119647 A1* | 4/2015 | Vaillancourt | A61B 17/0293 600/208 |

* cited by examiner

WOUND PROTECTOR

This application is a Continuation-in-Part of application Ser. No. 14/523,157 filed Oct. 24, 2014.

This invention relates to a wound protector.

As is known, wound protectors of a type as described in U.S. Pat. No. 8,231,527 are used, in particular, to provide access to internal tissue through open surgical procedures and endoscopic surgical procedures. As described, the wound protector is formed of a pair of rings with a flexible sleeve secured between the two rings. When used, the wound protector in positioned in a patient's abdominal wall through an incision. The distal ring is held in a collapsed position and then inserted through the incision. After insertion, the distal ring is released and then expands to its ring-like shape. The proximal ring is roliable to gather the flexible sleeve around the proximal ring and the wound proximal ring sits on the cutaneous surface of the abdominal wall. Shortening of the sleeve pulls the sleeve taut against the incised wound.

Rolling of the proximal ring of the known wound protectors can be cumbersome for a user, particularly where the ring is to rest against the patient.

Accordingly, it is an object of the invention to provide a wound protector that can positioned in a patient by a single practitioner.

It is another object of the invention to provide a wound protector that can be efficiently put in place in a patient.

It is another object of the invention to provide a wound protector that can be readily manipulated to achieve a secure position within an incision in a patient.

It is another object of the invention to provide a wound protector that can be used for large incisions.

Briefly, the invention provides a wound protector comprised of a collapsible distal ring; a flexible sleeve extending from the distal ring and having a loop at one end thereof; and an expansion member disposed within the loop of the flexible sleeve for movement between a collapsed state and an extended state, wherein movement of the expansion member into the extended state expands the loop peripherally while drawing the distal ring and the expansion member towards each other.

The wound protector is suitable for use in any procedure where a wound needs to be held open and kept clean.

In accordance with the invention, the expansion member includes a pair of U-shaped mutually telescoping units that define a square shape in the collapsed state of the member and a rectangular shape in the extended state of the member.

The flexible sleeve forms a frusto-conical shape between the distal ring and expansion member when not in use and with the expansion member in the collapsed state. Thus, the wound protector may be easily collapsed into a flattened condition for packaging purposes.

The wound protector also has locking means for selectively locking the two units of the expansion member against movement relative to each other when in use.

In use, the wound protector may be deployed, for example, as described in U.S. Pat. No. 8,231,527 in a patient's abdominal wall through an incision. In this case, the distal ring is held in a collapsed position to reduce its size and then inserted through the incision. After insertion, the distal ring is released to allow the ring to expand to a ring shape and to seat against the peritoneal surface of the abdominal wall.

After the distal ring is positioned within the patient, the expansion member is expanded into an extended state and to lie against the abdomen of the patient. At this time, the otherwise slack flexible sleeve is drawn tight against the wound made by the incision and the locking means is activated to lock the two units of the expansion member against relative movement, and particularly against a return movement.

These and other objects and advantages of the invention will become more apparent from the following detailed description taken in conjunction with the accompanying drawings wherein.

Figure 1:
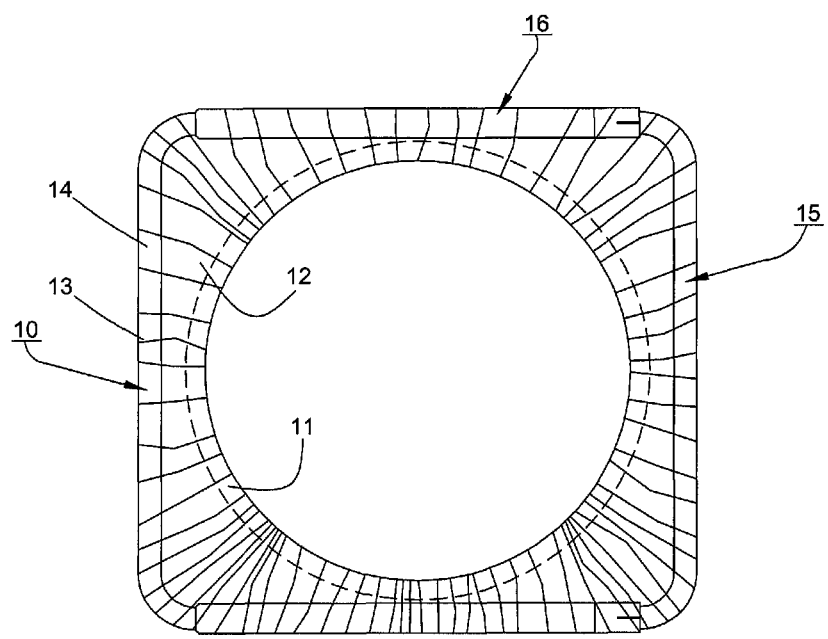
FIG. 1 depicts a top view of a wound protector of the invention with the expansion member in a collapsed state.
Figure 2:
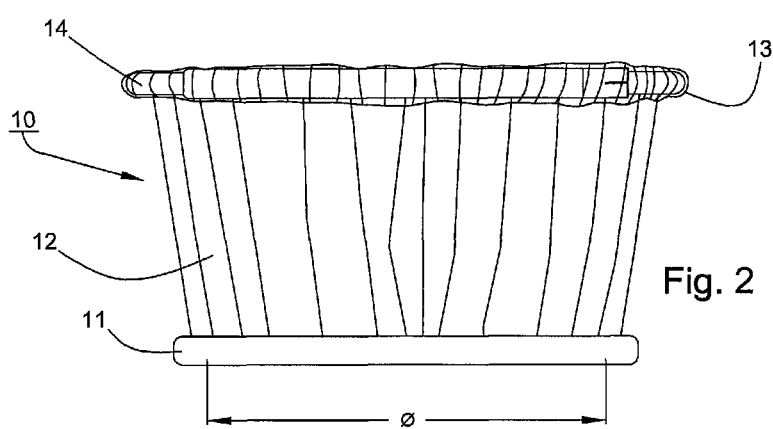
FIG. 2 illustrates a side view of the wound protector of FIG. 1 with the expansion member in a collapsed state.

Referring to FIGS. 1 and 2, the wound protector 10 comprises a collapsible distal ring 11, a flexible sleeve 12 (bag) extending from the distal ring 11 and having a loop 13 at one end and an expansion member 14 (frame) disposed within the loop 13 for movement between a collapsed state and an extended state.

Figure 3:
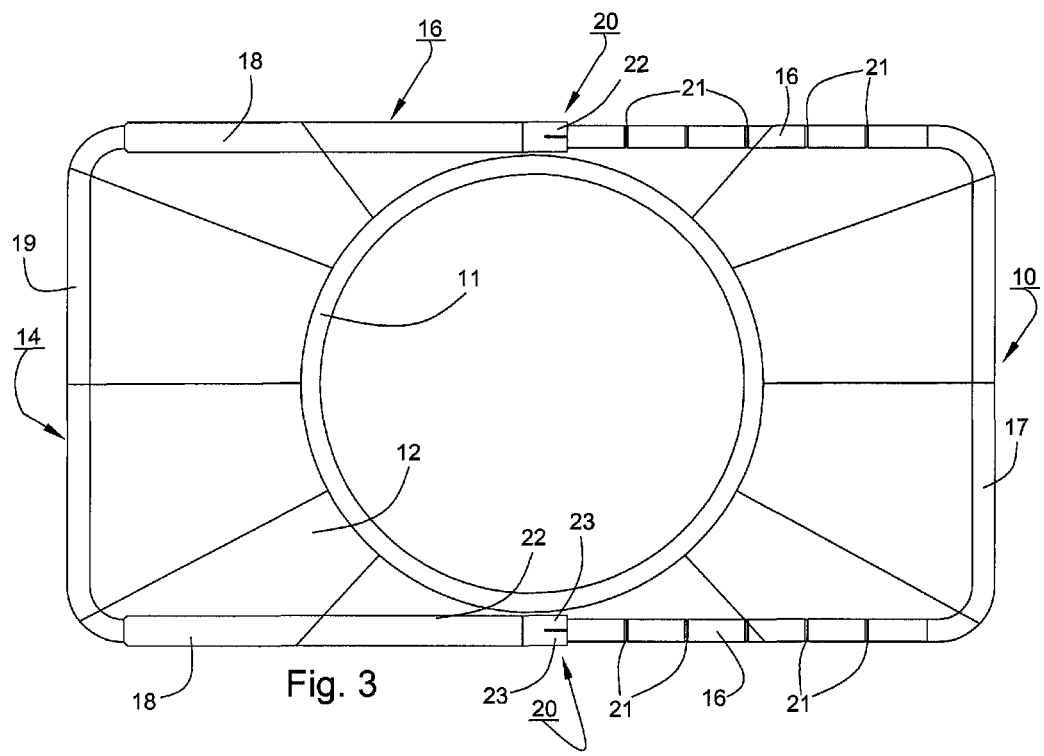
FIG. 3 illustrates a top view of the wound protector of FIG. 1 with the expansion member in an extended state.
Figure 4:
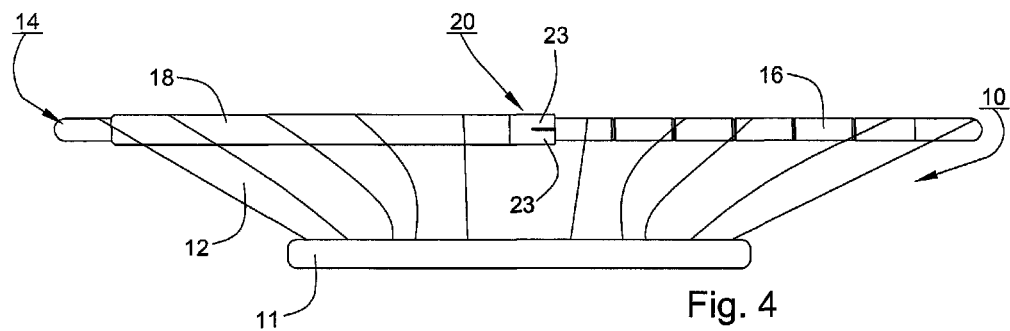
FIG. 4 illustrates a side view of the wound protector of FIG. 3.

Referring to FIGS. 3 and 4, wherein like reference characters indicate like parts as above, movement of the expansion member 14 from the collapsed state of FIG. 1 into the extended state of FIGS. 3 and 4 expands the loop 13 peripherally while drawing the distal ring 11 and the expansion member 14 towards each other.

Referring to FIGS. 1 and 2, the distal ring 11 is made of any suitable material, such as urethane, and is of solid cross-section while being of fixed diameter. The distal ring 11 is resiliently flexible in order to be inserted into an incision in a patient in the usual manner. The flexible sleeve 12 is made from a sheet of material, such as a urethane film, that is looped at the upper end, as viewed, to envelop the expansion member 14, overlaid on itself along a longitudinal seam (not shown) and secured as by welding to the distal ring 11. Since the distal ring 11 and expansion member 14 are of different sizes in the collapsed state of the expansion member 14, the sleeve 12 takes on a frusto-conical shape as viewed in FIG. 2.

Referring to FIGS. 1 and 3, the expansion member 14 includes a pair of U-shaped mutually telescoping units 15, 16 that define a square shape in the collapsed state of FIG. 1 and a rectangular shape in the extended state of FIG. 3. The size of the expansion member 14 in the collapsed state of FIG. 1 is slightly larger than the diameter of the distal ring 11 in one direction and still larger in the direction in which the expansion member 14 is to be extended.

Referring to FIG. 3, the U-shaped unit 15 of the expansion member 14 includes a pair of parallel arms 16 of solid cross-section and a rectilinear rod 17 integral with and between the two arms 16. The other unit 16 includes a pair of parallel arms 18 of tubular cross-section receiving the arms 16 of the first unit 15 in telescoping relation as well as a rectilinear rod 19 integral with and between the two arms 18.

A locking means 20 for selectively locking the units 15, 16 against movement relative to each other includes a plurality of longitudinally spaced grooves 21 on each arm 16 of the first unit 15 and a pair of rings 22 on the other unit 16. As illustrated, each ring 22 is secured coaxially to an end of a respective arm 18 of the second unit 16 and has at least one resilient finger 23, for example four equi-spaced resilient fingers 23.

Figure 5:
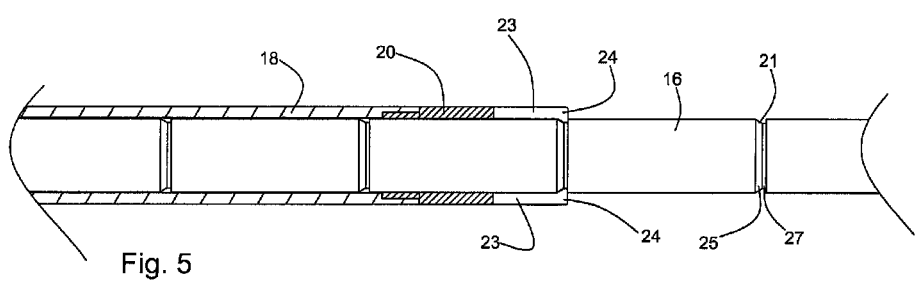
FIG. 5 illustrates a partial cross-sectional view of the locking means used in the wound protector of FIG. 1 in a locking position.
Figure 6:
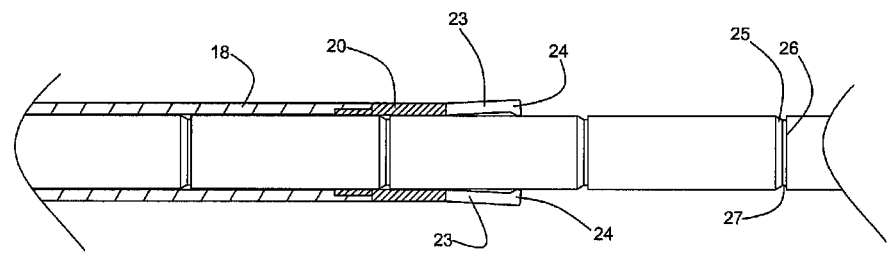
FIG. 6 illustrates a partial cross-sectional view of the locking means of FIG. 5 in an unlocked state.

As illustrated in FIG. 5, each finger 23 has a radially inwardly directed detent 24 of triangular shape at an end for selectively engaging in a selected groove 21 of the first unit 15. Also, each groove 21 is of a cross-section that allows a detent 24 to move out of the groove 21 in only one direction, i.e. the direction of expansion of the expansion member 14. For example, each groove 21 is formed of a tapered side wall 25, a flat base 26 extending from the tapered side wall 25 and a vertical side wall 27 extending from the flat base 26. Thus, when a detent 24 mates within a groove 21, the detent 24 abuts the vertical side wall 27 and prevents the second unit 16 from moving into the collapsed state of the expansion member 14 as indicated in FIG. 5. However, continued movement of the second unit 16 relative to the first unit 15 into the extended state of the expansion member 14, causes the detent 24 to slide along the tapered side wall 25 and out of the groove 21 to slide along the arm 16 as indicated in FIG. 6.

Figure 7:
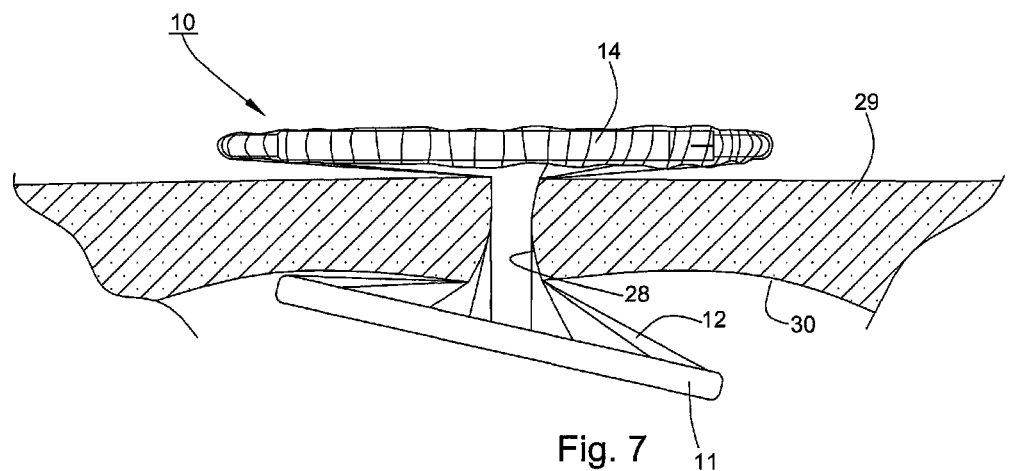
FIG. 7 illustrates a side view of the wound protector of FIG. 1 being placed within an incision in a patient with the expansion member in a collapsed state.

Referring to FIG. 7, wherein like reference characters indicate like parts as above, during use, after an incision 28 is made, for example, in an abdomen 29 of a patient and with the wound protector 10 in the collapsed state of FIG. 1, the distal ring 11 is held in a collapsed position by a practitioner to reduce its size and then inserted through the incision 28. After insertion, the distal ring 11 is released to allow the ring 11 to expand to a ring shape and to seat against the peritoneal surface 30 of the abdominal wall.

Figure 8:
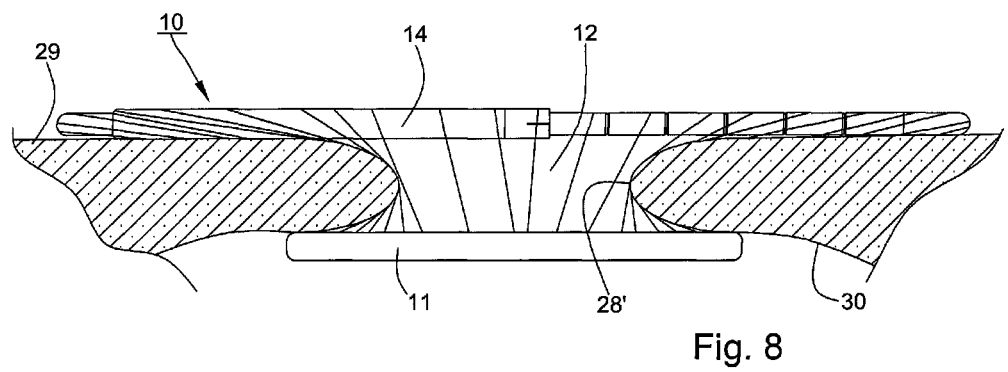
FIG. 8 illustrates a side view of the wound protector of FIG. 7 as placed within a patient with the expansion member in an extended state.

After placement of the distal ring 11 within the patient, the practitioner would expand the expansion member 14 into an extended state. During this procedure, the expanding expansion member comes to lie against the abdomen 29 of the patient while the otherwise slack flexible sleeve 12 is drawn tight against the wound 28' made by the incision 28 that has expanded as indicated in FIG. 8.

Figure 9:
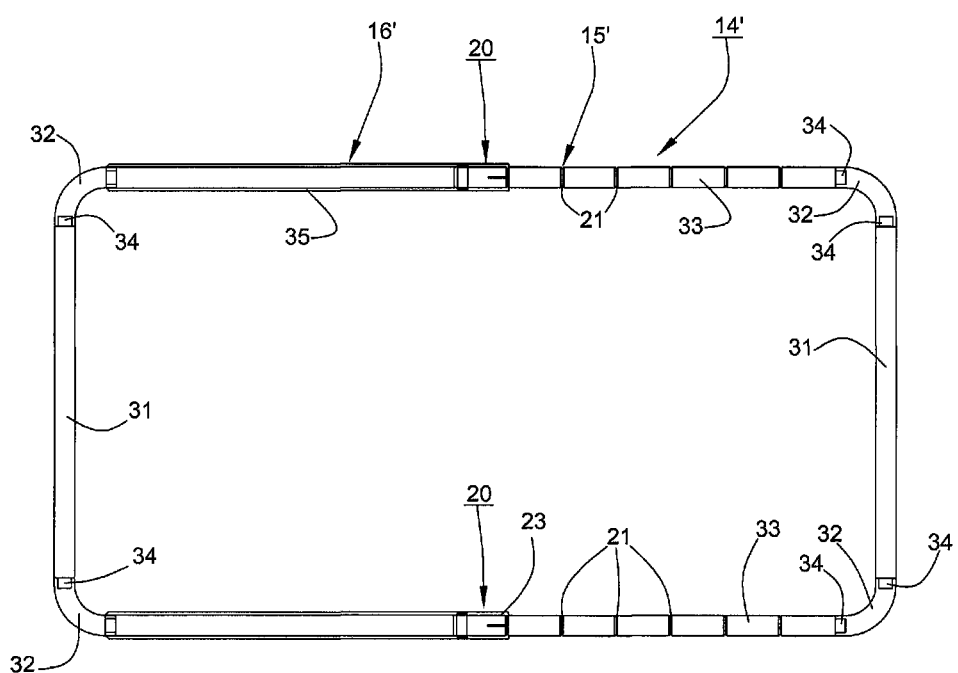
FIG. 9 illustrates a top view of modified expansion member in accordance with the invention.

Referring to FIG. 9 wherein like reference characters indicate like parts as above, the wound protector 10' may be made so as to accommodate different sizes of incisions. For example, the wound protector 10' is made with an expansion member 14' that includes a pair of U-shaped mutually telescoping units 15', 16' each made of separable and interchangeable parts. That is, a first unit 15' is made of a rectilinear rod 31, a pair of elbows 32 and a pair of parallel arms 33.

As illustrated, each elbow 32 is removably secured to one end of a respective arm 33 via a plug and socket connection 34 and releasably secured to a respective end of the rod 31 by a similar plug and socket connection 34. Thus, the rod 31 may be readily replaced by a rod of greater or smaller length in order to accommodate a distal ring (not shown) of a different diameter.

The second unit 16' is made in a similar manner of a rectilinear rod 31, a pair of elbows 32 and a pair of parallel arms 35 of tubular cross-section to receive the arms 33 of the first unit 15' in telescoping relation. As illustrated, each arm 35 is of larger diameter than an elbow 32 and is secured peripherally about an end of an elbow 32, as by welding, rather than being secured together by a plug and socket arrangement.

Figure 10:
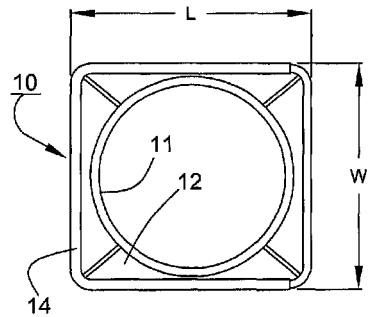
FIG. 10 illustrates a top view of a wound protector of the invention with the expansion member in a collapsed state.
Figure 11:
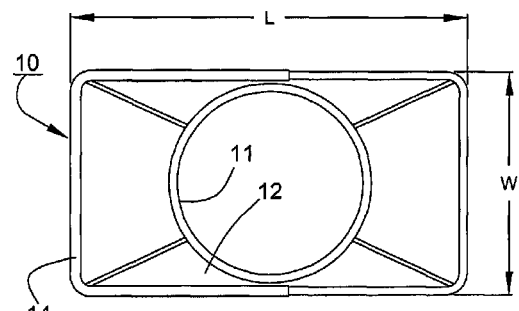
FIG. 11 illustrates a side view of the wound protector of FIG. 10 with the expansion member in a extended state.
Figure 12:
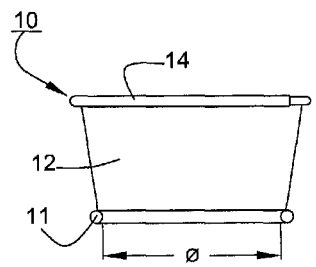
FIG. 12 illustrates a side view of the wound protector of FIG. 10.
Figure 13:
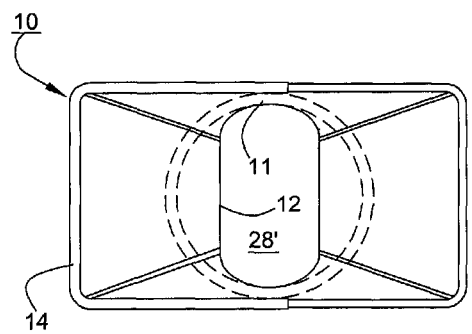
FIG. 13 illustrates a schematic view of the wound protector in an incision of a patient.

Referring to FIGS. 10 to 14, by way of example, the wound protector may have the following dimensions:

| Frame Identification | FIG. 10 Frame (Closed) (L × W) | FIG. 11 Frame (Open) (L × W) | FIG. 12 Bag Height (closed) | FIG. 12 Bottom Ring (ID) | FIG. 13 Opening in 1.75" Thick Simulated Skin with Frame Open |
|---|---|---|---|---|---|
| 5" | 8.4" × 7.9" | 14.4" × 7.9" | 5.5" | 5.187" | 5.187" |
| 6" | 8.4" × 7.9" | 14.4" × 7.9" | 5.5" | 6.187" | 6.187" |
| 7" | 8.4" × 7.9" | 14.4" × 7.9" | 5.5" | 7.187" | 6.75" |

Figure 14:
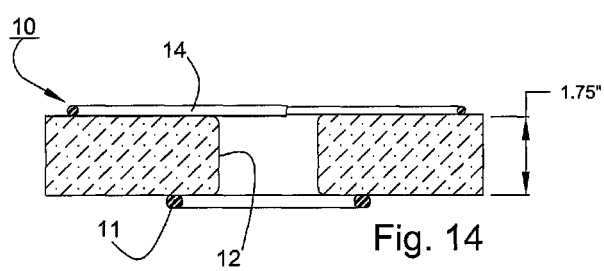
FIG. 14 illustrates a part cross-sectional view of the wound protector of FIG. 13.

Referring to FIGS. 13 and 14, when the wound protector 10 is in the extended state, the wound 28' made by the incision 28 is expanded. For example, for a 7" frame as set forth in the above table, if the depth of the incision is 1.75 inches and the bottom ring 11 has an inside diameter of 7.187 inches, the wound 28' would open to a total of 6.75 inches wide.

When in a compacted state for storage and/or shipment, the flexible sleeve 12 of the wound protector 10 is collapsed between the ring 11 and expansion member 14 into an annular shape.

What is claimed is:

1. A wound protector comprising
a collapsible distal ring of resiliently flexible material;
a flexible sleeve extending from said distal ring and having a loop at one end thereof; and
an expansion member disposed within said loop of said flexible sleeve for movement between a collapsed state and an extended state, wherein movement of said expansion member into said extended state expands said loop peripherally while drawing said distal ring and said expansion member towards each other, said expansion member including a pair of U-shaped mutually telescoping units wherein one of said units includes a pair of parallel arms of solid cross-section and the other of said units includes a pair of parallel arms of tubular cross-section receiving said arms of said one unit in telescoping relation.

2. A wound protector as set forth in claim 1 further comprising locking means for selectively locking said one of said units against movement relative to said other of said units.

3. A wound protector as set forth in claim 2 wherein said locking means includes a plurality of longitudinally spaced grooves on each said arm of said one of said units and a pair of rings on said other of said units, each said ring being secured to an end of a respective arm of said other of said units and having at least one resilient finger with a radially inwardly directed detent for selectively engaging in a selected groove of said one of said units.

4. A wound protector as set forth in claim 1 wherein each said unit includes a rectilinear rod, a pair of elbows and a pair of parallel arms, each said elbow of said pair of elbows being secured to one end of a respective arm of said pair of parallel arms and releasably secured to a respective end of said rod.

5. A wound protector as set forth in claim 1 wherein each said unit of said expansion member is made of a polycarbonate.

6. A wound protector comprising
a collapsible distal ring;
a flexible sleeve fixed to and extending from said distal ring and having a loop at one end thereof; and
an expansion member disposed within said loop of said flexible sleeve for movement between a collapsed state and an extended state, wherein movement of said expansion member into said extended state expands said loop peripherally while drawing said distal ring and said expansion member towards each other, said expansion member including a pair of U-shaped mutually telescoping units wherein one of said units includes a pair of parallel arms of solid cross-section and the other of said units includes a pair of parallel arms of tubular cross-section receiving said arms of said one unit in telescoping relation.

7. A wound protector as set forth in claim 6 further comprising locking means for selectively locking said one of said units against movement relative to said other of said units.

8. A wound protector as set forth in claim 6 further including a plurality of longitudinally spaced grooves on each said arm of said first unit and a pair of rings on said second unit, each said ring being secured coaxially to an end of a respective arm of said second unit and having at least one resilient finger with a radially inwardly directed detent at an end thereof for selectively engaging in a selected groove of said first unit for selectively locking said first unit against movement relative to said second unit.

9. A wound protector as set forth in claim 6 wherein said expansion member includes a first unit of separate and interchangeable parts including a rectilinear rod, a pair of elbows and a pair of parallel arms, each said elbow of said pair of elbows being releasably secured to one end of a respective arm of said pair of parallel arms and releasably secured to a respective end of said rod.

10. A wound protector as set forth in claim 9 wherein said expansion member includes a second unit of separate and interchangeable parts including a rectilinear rod, a pair of elbows and a pair of parallel arms of tubular cross-section receiving said arms of said first unit in telescoping relation, each said elbow of said pair of elbows of said second unit being secured to one end of a respective arm of said second unit and releasably secured to a respective end of said rod of said second unit.

* * * * *